United States Patent
Yao

(10) Patent No.: US 10,383,523 B2
(45) Date of Patent: Aug. 20, 2019

(54) BASAL BODY TEMPERATURE MEASURING SYSTEM AND BASAL BODY TEMPERATURE MEASURING DEVICE

(71) Applicant: E3 Co., Ltd., Tokyo (JP)

(72) Inventor: Bingwei Yao, Tokyo (JP)

(73) Assignee: E3 CO., LTD, Tokyo (JP)

( * ) Notice: Subject to any disclaimer, the term of this patent is extended or adjusted under 35 U.S.C. 154(b) by 132 days.

(21) Appl. No.: 15/316,986

(22) PCT Filed: Mar. 22, 2016

(86) PCT No.: PCT/JP2016/058925
§ 371 (c)(1),
(2) Date: Dec. 7, 2016

(87) PCT Pub. No.: WO2017/163300
PCT Pub. Date: Sep. 28, 2017

(65) Prior Publication Data
US 2018/0153413 A1   Jun. 7, 2018

(51) Int. Cl.
*A61B 5/01* (2006.01)
*A61B 5/00* (2006.01)
(Continued)

(52) U.S. Cl.
CPC .............. *A61B 5/01* (2013.01); *A61B 5/1118* (2013.01); *A61B 5/4306* (2013.01);
(Continued)

(58) Field of Classification Search
CPC ....... A61B 5/01; A61B 5/1118; A61B 5/1116; A61B 5/1113; A61B 5/1123;
(Continued)

(56) References Cited

U.S. PATENT DOCUMENTS

2015/0216475 A1*  8/2015  Luna .................. A61B 5/02438
                                               600/301
2015/0316419 A1*  11/2015  Punnakkal ............... G01K 3/08
                                               702/131
(Continued)

FOREIGN PATENT DOCUMENTS

CN  103 815 878 A  5/2014
CN  204 636 322 U  9/2015
(Continued)

OTHER PUBLICATIONS

Machine translation of CN 103815878 (Year: 2014).*
Extended European Search Report dated Oct. 19, 2017 in EP 16800865.4.

*Primary Examiner* — Devin B Henson
(74) *Attorney, Agent, or Firm* — Polsinelli PC

(57) ABSTRACT

There are provided an information recording unit 13 for recording, in a storage medium 14, body temperature information to be measured by a temperature sensor 11 for a sleeping period in association with movement information to be detected by a movement detecting sensor 12 for the same sleeping period, and a basal body temperature specifying unit 15 for analyzing the movement information recorded in the storage medium 14 to detect a wake timing of a user and specifying, as a basal body temperature, body temperature information measured immediately before the wake timing, and a body temperature of the user can be measured in a resting state during sleeping and be thus recorded in the storage medium 14, and furthermore, the body temperature recorded immediately before waking can be specified as the basal body temperature.

7 Claims, 3 Drawing Sheets

(51) Int. Cl.
- *G01K 13/00* (2006.01)
- *A61B 5/11* (2006.01)
- *A61B 10/00* (2006.01)
- *G01P 13/00* (2006.01)

(52) U.S. Cl.
CPC .......... *A61B 5/4809* (2013.01); *A61B 5/4812* (2013.01); *A61B 10/0012* (2013.01); *G01K 13/002* (2013.01); *G01P 13/00* (2013.01); *A61B 5/1123* (2013.01); *A61B 2010/0019* (2013.01)

(58) Field of Classification Search
CPC ... A61B 5/4306; A61B 5/4812; A61B 5/4806; A61B 5/4809; A61B 10/0012; A61B 2010/0019; G01K 13/002
See application file for complete search history.

(56) References Cited

U.S. PATENT DOCUMENTS

| | | | |
|---|---|---|---|
| 2018/0192873 A1* | 7/2018 | Chausiaux | A61B 5/6831 |
| 2018/0214028 A1* | 8/2018 | Zhang | G01K 1/14 |

FOREIGN PATENT DOCUMENTS

| | | | |
|---|---|---|---|
| CN | 105 105 719 A | 12/2015 | |
| JP | S63-260542 A | 10/1988 | |
| JP | H05-228116 A | 2/1993 | |
| JP | H11 47136 A | 2/1999 | |
| JP | 2005-164405 A | 6/2005 | |
| JP | 2012-220287 A | 11/2012 | |
| JP | 2014-233585 A | 12/2014 | |
| WO | WO-2010/098022 A1 | 9/2010 | |

\* cited by examiner

BASAL BODY TEMPERATURE MEASURING SYSTEM AND BASAL BODY TEMPERATURE MEASURING DEVICE

CROSS REFERENCE TO RELATED APPLICATIONS

This application is a National Phase filing under 35 U.S.C. § 371 of PCT/JP2016/058925 filed on Feb. 18, 2016. The entire contents of this application are hereby incorporated by reference.

TECHNICAL FIELD

The present invention relates to a basal body temperature measuring system and a basal body temperature measuring device, and more particularly to a device and system for measuring a basal body temperature in attachment to a body of a user for a sleeping period.

BACKGROUND ART

A human basal body temperature represents a body temperature measured in a resting state in which a factor of a change in a body temperature caused by activity is eliminated and only a minimum energy required for life support is consumed. In the case of women, the basal body temperature is closely related to an ovulation cycle. For this reason, the basal body temperature is utilized for various purposes, for example, reference of a woman who desires pregnancy or nonpregnancy, analysis of the cause of irregular menstruation or observation of progress thereof, and the like. Recently, the basal body temperature is utilized for a beauty, regulation of a health condition or the like in some cases.

Usually, the basal body temperature of a woman is changed periodically between approximately 0.3 to 0.5 degree except for the case of a sickness or heavy stress. By measuring the basal body temperature every day to know a rhythm (a change in a body temperature), it is possible to grasp a condition of a body such as presence of ovulation, a period of menstruation or a period likely to get pregnant.

It is necessary to accurately capture a fine change in a value. For this reason, the basal body temperature is usually measured in a body resting state. As a specific measuring method, it is recommended to perform measurement in a state in which a user is lying down in bed when a body has not been moved and an inner part of the body is taking a rest immediately after waking with enough sleeping.

Conventionally, there is proposed the technique for starting various sensors in a timing five minutes before a set time of an alarm clock (a standard time required for measuring a body temperature by a temperature sensor), deciding by these sensors whether the user is trying to measure a basal body temperature, and giving warning if there is a possibility that the measurement might be forgot (for example, see Patent Document 1).

According to the technique described in the Patent Document 1, the user can be promoted to measure the basal body temperature without forgetting it immediately after waking. Referring to the technique described in the Patent Document 1, however, the user measures the basal body temperature after the user is forcibly waken through an alarm clock or receives the warning from a device. For this reason, the measurement cannot be performed in a resting state.

On the other hand, there is also proposed the technique for going to bed with a body temperature measuring device attached to a housing pocket in underwear and measuring a basal body temperature and recording the basal body temperature in a memory during sleeping (for example, see Patent Document 2). The Patent Document 2 also describes that the sleep onset of a user is confirmed by the acceleration sensor and the measurement of a body temperature is then started by the temperature measuring element. According to the technique described in the Patent Document 2, it is possible to measure a basal body temperature in a resting state during sleeping.

Patent Document 1: Japanese Laid-Open Patent Publication No. 2012-220287
Patent Document 2: Japanese Laid-Open Patent Publication No. 2005-164405

DISCLOSURE OF THE INVENTION

Referring to the technique described in the Patent Document 2, however, the body temperature is continuously measured from sleep onset to wake-up. Therefore, it is impossible to specify which time zone for a body temperature is grasped to be suitable for a basal body temperature during that time. The body temperature is changed by a delicate movement such as turn-over. For this reason, the body temperature to be measured from the sleep onset to the wake fluctuates. In the case of the Patent Document 2, there is a problem in that it is impossible to specify which of the fluctuating body temperatures is grasped to be the basal body temperature.

The present invention has been made to solve the problems and has an object to enable accurate measurement of a basal body temperature in a resting state.

In order to attain the object, in the present invention, body temperature information to be measured by a temperature sensor for a sleeping period is recorded in a storage medium in association with movement information to be detected by a movement detecting sensor for the same sleeping period, and the movement information recorded in the storage medium is then analyzed to detect a wake timing of a user and body temperature information measured immediately before the wake timing is specified as a basal body temperature.

According to the present invention having the structure described above, the body temperature of the user can be measured in a resting state during sleeping and be recorded in the storage medium. In addition, the body temperature recorded immediately before waking can be specified as a basal body temperature. Therefore, it is possible to obtain an accurate basal body temperature measured in the resting state immediately before the waking.

BEST MODE FOR CARRYING OUT THE INVENTION (First Embodiment)

Figure 1:
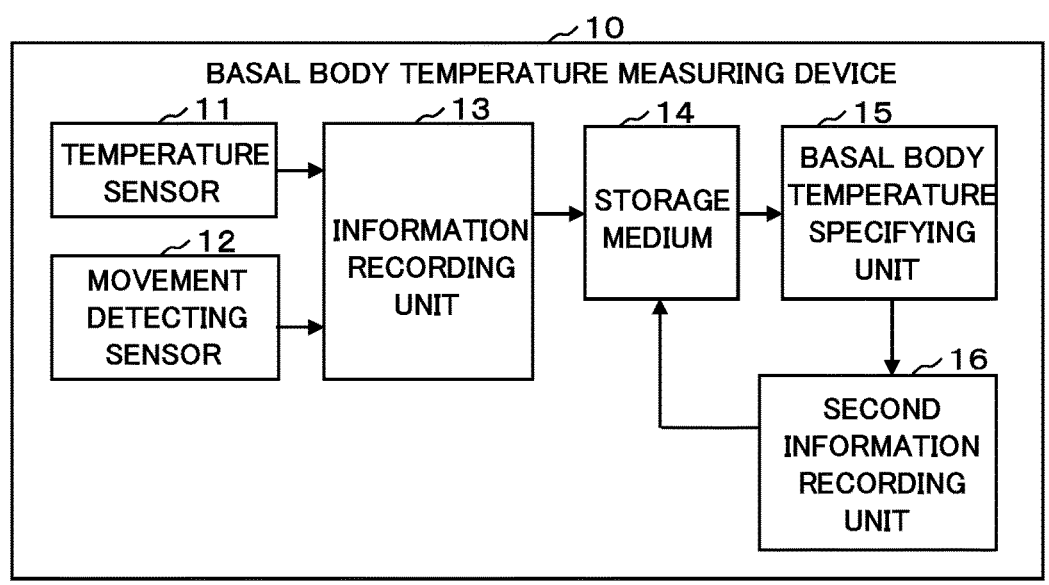
FIG. 1 is a block diagram showing an example of a functional structure of a basal body temperature measuring device according to a first embodiment.
Figure 2:
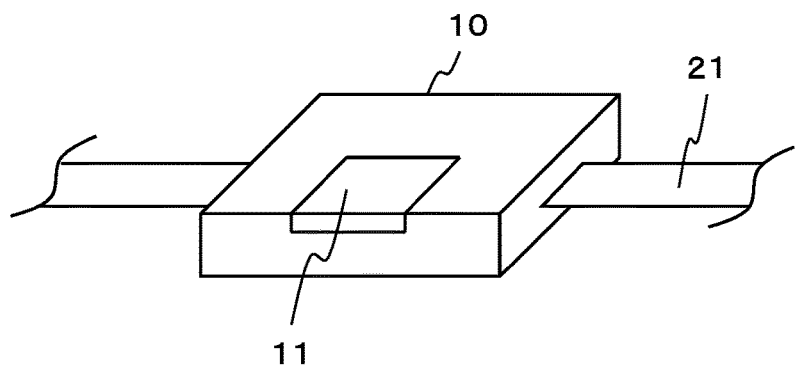
FIG. 2 is a view showing an example of an appearance structure of a basal body temperature measuring device according to first to third embodiments.

A first embodiment of the present invention will be described below with reference to the drawings. FIG. 1 is a block diagram showing an example of a functional structure of a basal body temperature measuring device according to the first embodiment. FIG. 2 is a view showing an example of an appearance structure of the basal body temperature measuring device according to the first embodiment.

A basal body temperature measuring device 10 according to the first embodiment is attached to a body of a user for a sleeping period to measure a basal body temperature. As shown in FIG. 2, a temperature sensor 11 is provided on a surface of a housing and the basal body temperature measuring device 10 is attached in such a manner that the temperature sensor 11 touches a body of a user. For example, the basal body temperature measuring device 10 is attached to measure a body temperature in such a manner that the temperature sensor 11 touches a breast or abdomen part of the user.

A belt 21 for fixing the basal body temperature measuring device 10 to a body is provided in such a manner that the basal body temperature measuring device 10 does not slip down from the body during sleeping. Although the belt 21 is used herein, a fixing method is not restricted thereto. For example, a tape or the like may be used to fix the basal body temperature measuring device 10 to the body.

As shown in FIG. 1, the basal body temperature measuring device 10 according to the first embodiment includes, as a functional structure thereof, the temperature sensor 11, a movement detecting sensor 12, an information recording unit 13, a storage medium 14, a basal body temperature specifying unit 15 and a second information recording unit 16. Function blocks of the information recording unit 13, the basal body temperature specifying unit 15 and the second information recording unit 16 can be configured from any of hardware, a DSP (Digital Signal Processor) and software.

For example, with a structure obtained by the software, each of the function blocks 13, 15 and 16 actually includes a CPU, an RAM, an ROM and the like in a computer and is implemented by an operation of a program stored in a storage medium such as an RAM, an ROM, a hard disk or a semiconductor memory. The storage medium for storing the program may be the same as the storage medium 14 or different therefrom.

The temperature sensor 11 measures a temperature of a body of a user during sleeping. The movement detecting sensor 12 detects a movement of the body of the user during sleeping. The movement detecting sensor 12 can be configured from an acceleration sensor as an example. When the body of the user is moved, the acceleration sensor detects an acceleration generated in the movement and outputs acceleration information.

The information recording unit 13 records, in the storage medium 14, body temperature information to be measured by the temperature sensor 11 in association with the movement information (acceleration information) to be detected by the movement detecting sensor 12. The storage medium 14 is a nonvolatile storage medium such as a hard disk or a semiconductor memory.

The association of body temperature information and movement information can be performed through a measuring time, for example. Specifically, the information recording unit 13 records, in the storage medium 14, the body temperature information and the movement information input from the temperature sensor 11 and the movement detecting sensor 12 respectively together with a time stamp at a predetermined time interval (for example, an interval of 30 seconds).

Information to be used for the association of the body temperature information and the movement information is not restricted to the time stamp. For example, it is also possible to use a simple identifier such as a serial number issued sequentially every predetermined time interval from start of the measurement in place of the time stamp.

The basal body temperature specifying unit 15 analyzes the movement information recorded in the storage medium 14 to detect awake timing of the user and specifies body temperature information measured immediately before the wake timing as a basal body temperature.

Figure 3:
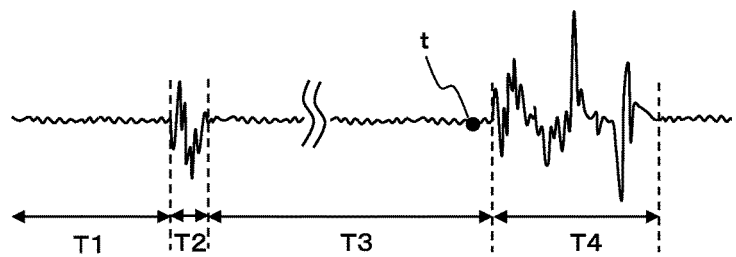
FIG. 3 is a chart showing an example of processing of a basal boy temperature specifying unit.

FIG. 3 is a chart showing an example of processing of the basal body temperature specifying unit 15. FIG. 3 shows acceleration information obtained in use of the acceleration sensor as the movement detecting sensor 12. For easy understanding as an image, acceleration information in time series obtained by the movement detecting sensor 12 is shown as a continuous waveform. However, the acceleration information is actually recorded, in the storage medium 14, as discrete data every 30 seconds.

For example, in the case in which the basal body temperature measuring device 10 is attached to the breast part of the user, acceleration information about a comparatively small amplitude is detected by the movement detecting sensor 12 in conformity with a breathing cycle through the movement of the breast part attendant on the breathing of the user and is recorded in the storage medium 14 through the information recording unit 13 (periods T1 and T3). The periods T1 and T3 are periods for which the user is sleeping at rest without moving user's body.

When the user turns over during sleeping, moreover, acceleration information about a comparatively great amplitude is detected by the movement detecting sensor 12 at that moment and is recorded in the storage medium 14 through the information recording unit 13 (the period T2). When the user wakes, furthermore, the acceleration information about a comparatively great amplitude is detected by the movement detecting sensor 12 for a long time and is recorded in the storage medium 14 through the information recording unit 13 (a period T4).

The basal body temperature specifying unit 15 detects, as the wake timing of the user, a start timing of the period T4 for which the acceleration information about a comparatively great amplitude continues for a long time based on the acceleration information shown in FIG. 3 which is recorded in the storage medium 14. Then, the basal body temperature specifying unit 15 specifies, as a basal body temperature, body temperature information measured at a timing t immediately before the wake timing. In other words, the body temperature information recorded in the storage medium 14 in association with a time stamp at the timing t is specified as the basal body temperature of the user.

The timing t is a timing included in the period T3 for which the user is in a resting state. By specifying, as the basal body temperature, a body temperature recorded at the timing t, accordingly, it is possible to obtain an accurate basal body temperature measured in a resting state in which the user is sleeping.

The basal body temperature specifying unit 15 notifies the second information recording unit 16 of the specified basal body temperature of the user. The second information recording unit 16 records the basal body temperature given from the basal body temperature specifying unit 15 in the storage medium 14 in association with calendar information representing a measurement date. By measuring and recording the basal body temperature every day, it is possible to grasp a rhythm of a change in the basal body temperature.

The information recorded in the storage medium 14 (the body temperature information and the movement information, and the specified basal body temperature information) can be output to an external computer which is not shown and be thus utilized. Alternatively, it is also possible to provide a display in the basal body temperature measuring device 10 itself, thereby visualizing and displaying the information recorded in the storage medium 14 graphically.

As described above in detail, in the first embodiment, the body temperature information to be measured by the temperature sensor 11 for the sleeping period is recorded in the storage medium 14 in association with the movement information to be detected by the movement detecting sensor 12 for the same sleeping period and the movement information recorded in the storage medium 14 is then analyzed to detect the wake timing of the user, and the body temperature information measured immediately before the wake timing is specified as the basal body temperature.

According to the first embodiment having such a structure, the body temperature of the user can be measured in a resting state during sleeping and be recorded in the storage medium 14, and furthermore, the body temperature recorded immediately before the waking can be specified as the basal body temperature. Therefore, it is possible to obtain an accurate basal body temperature measured in the resting state brought immediately before the waking.

As described above, there is a possibility that the basal body temperature might be changed even if a little body movement is performed. For this reason, it is desirable to acquire, as the basal body temperature, a body temperature when the user is sleeping and his (her) body is not being moved. However, the basal body temperature is conventionally measured after waking. Therefore, the basal body temperature cannot be measured in a real sense. On the other hand, according to the first embodiment, it is possible to measure a true basal body temperature.

Figure 4:
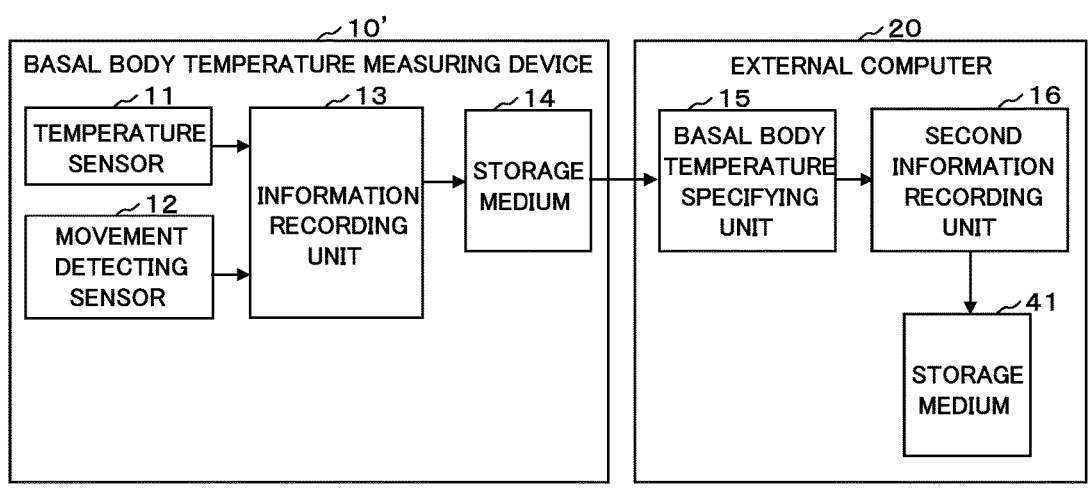
FIG. 4 is a block diagram showing an example of a structure of a basal body temperature measuring system according to the first embodiment.

Although the basal body temperature measuring device 10 includes all of the temperature sensor 11, the movement detecting sensor 12, the information recording unit 13, the storage medium 14, the basal body temperature specifying unit 15 and the second information recording unit 16 in the embodiment, the present invention is not restricted thereto. For example, as shown in FIG. 4, it is also possible to employ a system structure in which a portable basal body temperature measuring device 10' includes the temperature sensor 11, the movement detecting sensor 12, the information recording unit 13 and the storage medium 14 and an external computer 20 to be connected to the basal body temperature measuring device 10' by wireless or wire includes the basal body temperature specifying unit 15, the second information recording unit 16 and a storage medium 41.

In this case, the basal body temperature measuring device 10' and the external computer 20 can be connected through a cable such as a USB (Universal Serial Bus). Alternatively, both the basal body temperature measuring device 10' and the external computer 20 may include wireless communicating means such as Bluetooth (registered trademark) or a wireless LAN to enable wireless transmission of the information recorded in the storage medium 14 from the basal body temperature measuring device 10' to the external computer 20. Alternatively, both the basal body temperature measuring device 10' and the external computer 20 may include internet connecting means to enable upload of the information recorded in the storage medium 14 from the basal body temperature measuring device 10' to a server device (not shown) on internet and download of the information from the server device by the external computer 20.

(Second Embodiment)

Figure 5:
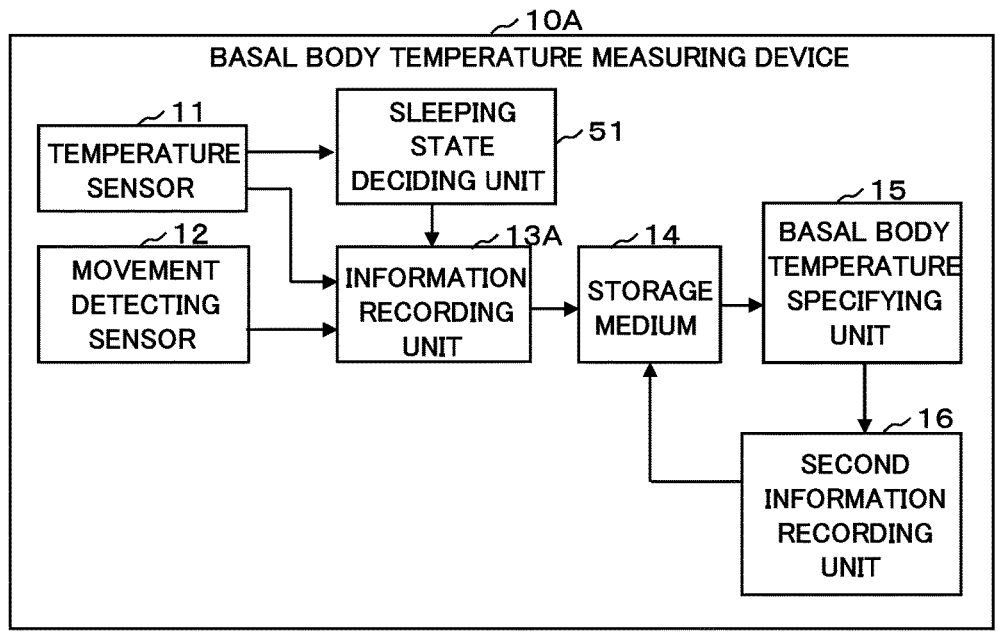
FIG. 5 is a block diagram showing an example of a functional structure of the basal body temperature measuring device according to the second embodiment.

Next, a second embodiment of the present invention will be described with reference to the drawings. FIG. 5 is a block diagram showing an example of a functional structure of a basal body temperature measuring device 10A according to the second embodiment. In FIG. 5, since components having the same reference numerals as those shown in FIG. 1 have the same functions, repetitive description will be omitted. An appearance structure of the basal body temperature measuring device 10A is the same as that in FIG. 2.

As shown in FIG. 5, the basal body temperature measuring device 10A according to the second embodiment further includes a sleeping state deciding unit 51 as the functional structure. Moreover, an information recording unit 13A is provided in place of the information recording unit 13.

The sleeping state deciding unit 51 decides whether the user is in a REM sleeping state or non-REM sleeping state based on body temperature information to be measured by a temperature sensor 11. The REM sleeping represents a state in which a body is sleeping and a brain is waking, that is, a state in which sleeping is light. The non-REM sleep represents a state in which the brain is sleeping, that is, a state in which sleeping is deep.

It is known that the REM sleep and non-REM sleep and the body temperature have a correlation. In other words, when a human first falls asleep, the body temperature rapidly falls by approximately one degree and moves into the non-REM sleep to be a deep sleep. When approximately 90 minutes pass, thereafter, a transition to the REM sleep which is a light sleep is made. A rhythm of the non-REM sleep and the REM sleep is set to be a single sleeping cycle which is repeated four to five times in one night. A period for the REM sleep is short, that is, approximately 2 to 3 minutes in an initial sleep cycle and is increased every time the sleep cycle is repeated.

Also after the body temperature rapidly falls by approximately one degree immediately after falling asleep, the body temperature slightly rises or falls. In the movement into the non-REM sleep, a sweating function becomes active so that the body temperature falls. On the other hand, when the non-REM sleep is changed to the REM sleep, the body temperature rises. Accordingly, the sleeping state deciding unit 51 can decide whether a user is in the REM sleeping state or the non-REM sleeping state by monitoring whether the body temperature measured by the temperature sensor 11 is in a falling state or a rising state.

The information recording unit 13A starts to record the body temperature information and the movement information in the storage medium 14 when it is decided by the sleeping state deciding unit 51 that a transition from the non-REM sleeping state to the REM sleeping state has been made. In the case in which the user naturally wakes without using an alarm clock or the like, there is a high possibility that user might wake for a period of the REM sleep which is a light sleep. When the record into the storage medium 14 is started when the transition from the non-REM sleeping state to the REM sleeping state is detected, therefore, it is possible to measure and record a basal body temperature in a resting state immediately before waking without performing unnecessary record as much as possible.

Since the REM sleep occurs four to five times during sleeping in one night, the record into the storage medium 14 may be started when the transition to a fourth REM sleep is detected, for example. In consideration of how many sleeping cycles are included during a sleeping time scheduled by the user, alternatively, the user may designate the start of the record since an n-th (n is a desirable value of 1 to 5) REM sleep for the basal body temperature measuring device 10A. As another example, moreover, it is also possible to perform a recording operation into the storage medium 14 for each REM sleeping period and to prevent the recording operation from being performed for each non-REM sleeping period.

Although the description has been given to the example in which the REM sleeping state/non-REM sleeping state is decided based on the body temperature information to be measured by the temperature sensor 11 in the second embodiment, it is also possible to decide the REM sleeping state/non-REM sleeping state based on the movement information to be detected by the movement detecting sensor 12 in place of or in addition to the body temperature information.

As described above, the REM sleep represents a state in which the body is sleeping and the brain is waking. For this reason, the body is rarely moved during the REM sleep. On the other hand, the non-REM sleep represents a state in which the brain is sleeping, and a muscle supporting the body is being used so that turn-over can be performed. Accordingly, the sleeping state deciding unit 51 can decide whether the user is in the REM sleeping state or the non-REM sleeping state by monitoring whether the movement of the body is detected by the movement detecting sensor 12.

Also in the second embodiment, in the same manner as in FIG. 4, it is also possible to employ a system structure including a basal body temperature measuring device 10A' having a temperature sensor 11, a movement detecting sensor 12, an information recording unit 13A, a storage medium 14 and a sleeping state deciding unit 51, and an external computer 20 having a basal body temperature specifying unit 15, a second information recording unit 16 and a storage medium 41.

(Third Embodiment)

Figure 6:
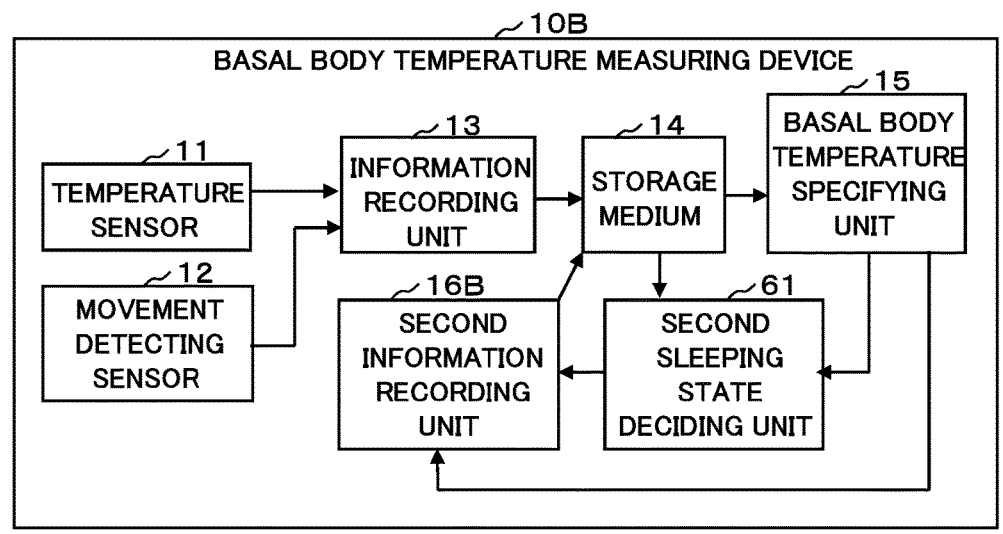
FIG. 6 is a block diagram showing an example of a functional structure of the basal body temperature measuring device according to the third embodiment.

Next, a third embodiment of the present invention will be described with reference to the drawings. FIG. 6 is a block diagram showing an example of a functional structure of a basal body temperature measuring device 10B according to the third embodiment. In FIG. 6, since components having the same reference numerals as those shown in FIG. 1 have the same functions, repetitive description will be omitted. An appearance structure of the basal body temperature measuring device 10B is the same as that in FIG. 2.

As shown in FIG. 6, the basal body temperature measuring device 10B according to the third embodiment further includes a second sleeping state deciding unit 61 as a functional structure thereof. Moreover, a second information recording unit 16B is provided in place of the second information recording unit 16.

The second sleeping state deciding unit 61 decides whether a user has been in a REM sleeping state or a non-REM sleeping state in a measurement timing (a timing t in FIG. 3) of a basal body temperature specified by a basal body temperature specifying unit 15 based on at least one of body temperature information and movement information which are recorded in a storage medium 14. The deciding method is the same as described in the second embodiment. The second sleeping state deciding unit 61 notifies the second information recording unit 16B of the decided sleeping state.

The second information recording unit 16B records, in the storage medium 14, the basal body temperature specified by the basal body temperature specifying unit 15 together with information representing the sleeping state (either the REM sleeping state or the non-REM sleeping state) decided by the second sleeping state deciding unit 61.

As described above, in the case in which the user naturally wakes without using an alarm clock, there is a high possibility that the user might wake for a REM sleeping period in which sleeping is light. However, this does not always occur. By leaving, as record, whether the basal body temperature measured in the timing t is obtained during the REM sleep or the non-REM sleep, therefore, it is possible to grasp whether the recorded basal body temperature is a lower body temperature during the non-REM sleep or a higher body temperature during the REM sleep.

Also in the third embodiment, in the same manner as in FIG. 4, it is also possible to employ a system structure including a basal body temperature measuring device 10B' having a temperature sensor 11, a movement detecting sensor 12, an information recording unit 13 and a storage medium 14, and an external computer 20 having a basal body temperature specifying unit 15, a second information recording unit 16B, a storage medium 41 and a second sleeping state deciding unit 61.

Although the description has been given to the example in which the acceleration sensor is used as an example of the movement detecting sensor 12 and the wake timing of the user is detected based on the acceleration information shown in FIG. 3 in the first to third embodiments, the present invention is not restricted thereto. For example, it is also possible to use an angular velocity sensor (a gyro sensor) in place of or in addition to the acceleration sensor.

For example, in the case in which a posture of the user is detected by the gyro sensor, the posture is greatly changed when the user is lying down and sleeping and when he (she) is waking and standing up. For this reason, the basal body temperature specifying unit 15 can detect, as awake timing, a time that the posture is greatly changed and can specify, as a basal body temperature, body temperature information measured immediately before the wake timing.

In addition, all of the first to third embodiments are only illustrative for concreteness to carry out the present invention and the technical scope of the present invention should not be thereby construed to be restrictive. In other words, the present invention can be carried out in various configurations without departing from the gist or main features thereof.

EXPLANATION OF DESIGNATION

10, 10', 10A, 10B basal body temperature measuring device
11 temperature sensor
12 movement detecting sensor
13, 13A information recording unit
14 storage medium
15 basal body temperature specifying unit
16, 16B second information recording unit
20 external computer
51 sleeping state deciding unit
61 second sleeping state deciding unit

The invention claimed is:

1. A basal body temperature measuring system including a device for measuring a basal body temperature in attachment to a body of a user for a sleeping period, the system comprising:
   a temperature sensor for measuring a temperature of the body;
   a movement detecting sensor for detecting a movement of the body;
   an information recording unit for recording, in a storage medium, body temperature information to be measured by the temperature sensor in association with movement information to be detected by the movement detecting sensor; and
   a controller programmed to:
      identify, based at least on the recorded movement information, when the user awoke from the sleeping period;
      set as the basal body temperature for the sleeping period the temperature of the user immediately before the identified awakening.

2. The basal body temperature measuring system according to claim 1, further comprising a second information recording unit for recording, in a storage medium, the basal body temperature specified by the controller.

3. The basal body temperature measuring system according to claim 1,
   further comprising a sleeping state deciding unit for deciding whether the user is in a REM sleeping state or a non-REM sleeping state based on at least one of the body temperature information to be measured by the temperature sensor and the movement information to be detected by the movement detecting sensor,
   the information recording unit starts to record the body temperature information and the movement information into the storage medium when it is decided by the sleeping state deciding unit that a transition from the non-REM sleeping state to the REM sleeping state has been made.

4. The basal body temperature measuring system according to claim 1,
   further comprising a sleeping state deciding unit for deciding whether the user has been in a REM sleeping state or a non-REM sleeping state in a measurement timing of the basal body temperature specified by the controller based on at least one of the body temperature information and the movement information which are recorded in the storage medium.

5. The basal body temperature measuring system according to claim 4,
   further comprising a second information recording unit for recording, in a storage medium, the basal body temperature specified by the controller together with information representing a sleeping state decided by the second sleeping state deciding unit.

6. The basal body temperature measuring system according to claim 1, wherein the temperature sensor, the movement detecting sensor, the storage medium and the information recording unit are provided in a portable basal body temperature measuring device, and the controller is provided in an external computer to be connected to the basal body temperature measuring device by wireless or wire.

7. The basal body temperature measuring system according to claim 1,
   wherein the movement detecting sensor is an acceleration sensor for outputting acceleration information in response to the movement of the body,
   the information recording unit records, in the storage medium, the body temperature information to be measured by the temperature sensor in association with the acceleration information to be detected by the acceleration sensor, and
   the controller detects when the user awakens based on the acceleration information being consistent with waking body movements.

* * * * *